United States Patent [19]

Tsou

[11] Patent Number: 5,378,456
[45] Date of Patent: Jan. 3, 1995

[54] ANTITUMOR MITOXANTRONE POLYMERIC COMPOSITIONS

[75] Inventor: Hwei-Ru Tsou, New City, N.Y.

[73] Assignee: American Cyanamid Company, Wayne, N.J.

[21] Appl. No.: 37,149

[22] Filed: Mar. 25, 1993

[51] Int. Cl.$^6$ ............................ A61K 31/74; A61K 47/48
[52] U.S. Cl. ................................. 424/78.3; 424/78.33
[58] Field of Search ................ 424/78.36, 78.3, 78.33

[56] References Cited

U.S. PATENT DOCUMENTS

| 4,520,162 | 5/1985 | Hirano et al. | 525/327.6 |
| 4,871,528 | 10/1989 | Tognella et al. | 514/922 |

FOREIGN PATENT DOCUMENTS

| 902344 | 9/1985 | Belgium. |
| 0393575 | 4/1990 | European Pat. Off.. |
| 60-67426 | of 1985 | Japan. |
| 60-67490 | of 1985 | Japan. |

OTHER PUBLICATIONS

Mohr et al., Canc. Res. 35: 3750-3754, Dec. 1975, "Pyran Copolymer as an Effective Adjuvant to Chemotherapy against a Murine Leukemia and Solid Tumor."
Pryzybylski et al., Canc. Treat. Reports vol. 62, No. 11, Nov. 1978, "DIVEMA-Methotrexate: Immune-Adjuvant Role of Polymeric Carriers Linked to Antitumor Agents."
Zunino et al., Canc. Treat. Reports vol. 71, No. 4, Apr. 1987, "Increased Therapeutic Efficacy and Reduced Toxicity of Doxorubicin Linked to Pyran Copolymer...".
Zaharko et al., Canc. Treat. Reports, vol. 68, No. 10, Oct. 1984, "Effects of 5-Aza-2'-deoxycytidine in combination with the Biochemical Modulator...".
Fung et al., JNCI. vol. 62, No. 5, May 1979, "In Vitro Inhibitory Effects of Polymer-Linked Methotrexate Derivatives on Tetrahydrofolate Dehydrogenase...".
Pryzybylski et al., Makromol. Chem. 179: 1719-1733, (1978), "Syntheses and Characterization of Polymeric Derivatives of the Antitumor Agent Methotrexate."
Hirano et al., Makromol. Chem. 187: 2815-2824, (1986), "Synthesis of Antitumor-Active Conjugates of Adriamycin or Daunomycin with the Copolymer of Divinyl Ether and...".
Dunn et al., Amer. Chem. Soc., ACS Symposium Series 469, 1990, Polymeric Drugs and Drug Delivery Systems.

*Primary Examiner*—Thurman K. Page
*Assistant Examiner*—Peter Kulkosky
*Attorney, Agent, or Firm*—Kenneth J. Dow

[57] ABSTRACT

An antitumor polymeric composition comprising an anthracene antitumor compound, particularly mitoxantrone, covalently conjugated to, or admixed with, a divinyl ether-maleic anhydride (MVE) copolymer and methods of treating solid tumors and inducing regression of leukemia cell growth in mammals by administering such compositions.

4 Claims, 2 Drawing Sheets

ANTITUMOR MITOXANTRONE POLYMERIC COMPOSITIONS

BACKGROUND OF THE INVENTION

1. Field of the Invention

The present invention relates to novel antitumor polymeric compositions and methods of treatment therewith. More particularly, the invention relates to a pharmaceutical composition comprising an anthracene antitumor compound, particularly mitoxantrone, covalently conjugated to, or admixed with, a divinyl ether-maleic anhydride (MVE) copolymer.

2. Description of the Related Art

Macromolecules have been used as drug carriers in an attempt to prolong plasma levels of drugs presumably as a result of slow release of drugs from macromolecules and to achieve favorable uptake by the tumor cells. Among macromolecular carriers, divinyl ether-maleic anhydride (MVE) has been investigated extensively. MVE copolymer contains multiple anhydride rings, which allows easy functionalization with antitumor agents carrying nucleophilic groups such as —NH$_2$, —OH and —SH. Furthermore, a carboxyl group is generated from each anhydride ring functionalized with a drug molecule. Therefore, MVE copolymer is capable of covalently binding a large number of lipophilic antitumor agents, while maintaining water solubility.

MVE copolymer has been covalently linked with various therapeutically active antitumor agents including 5-fluorouridine, daunomycin, adriamycin, β-D-arabinofuranosylcytosine and methotrexate with varying results. Some of the MVE-linked agents demonstrated higher therapeutic efficacies and lower toxicities during in vivo antitumor evaluations while others showed no increase or were unstable under physiological conditions. MVE linked with methotrexate through the 2- or 4-amino groups of the pteridine ring of methotrexate showed only a slight increase in life span (% ILS) against L1210 leukemia in mice when compared with free methotrexate. MVE copolymer had a potentiating effect on the antitumor activity of 5-aza-2'-deoxycytidine but had no therapeutic benefit when used with cyclophosphamide under the same experimental conditions of tumor burden and treatment schedule. D. S. Zaharko et al., Canc. Treat. Rpts. 68(10): 1255-1264 (1984). U.S. Pat. No. 4,520,162 discloses MVE-copolymer conjugates of adriamycin, daunomycin and AraC.

The anthracene antitumor agents are a group of compounds having an anthracene moiety of which mitoxantrone and bisantrene are representative members. Mitoxantrone is indicated for treatment of acute non-lymphocytic leukemia in humans. While these agents exhibit excellent anti-tumor activity, they also exhibit strong toxicity to normal cells. For example, administration of mitoxantrone is associated with myelosuppression and cardiac abnormalities as well as other side effects. Therefore, any potentiation of the drug's antitumor effect would theoretically allow smaller doses of the drug to be administered over longer periods of time thereby avoiding or minimizing some of the undesirable adverse effects. It is therefore an object of the present invention to provide a method of potentiating the antitumor activity of such anthracene antitumor agents.

SUMMARY OF THE INVENTION

The invention is directed to therapeutically active antitumor compositions comprising a synthetic anthracene antineoplastic compound covalently conjugated with, or in admixture with, a hydrolyzate of a copolymeric moiety of divinyl ether and maleic anhydride (MVE). The copolymeric MVE moiety may be expressed by the general formula:

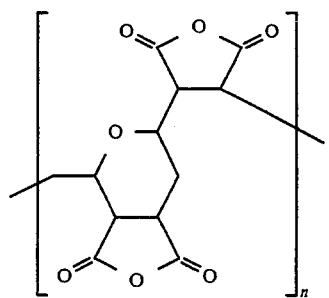

where n is an integer of at least 2. The anthracene antineoplastic compound is selected from the known antineoplastic compounds having an anthracene moiety such as mitoxantrone, bisantrene and homologs, isomers and analogs thereof. The compositions of the present invention, containing the MVE copolymer in admixture with or covalently conjugated to the anthracene compound, show higher antitumor activity than either agent exhibits when administered alone.

As stated above, the MVE copolymer of general formula I may be admixed with, or covalently conjugated to the anthracene antitumor agent. The covalent linkage between the MVE copolymer and the anthracene antitumor agent is formed between the carbonyl group of the maleic anhydride moiety of the polymer and the amino group of the anthracene antitumor agent. When the anthracene agent is mitoxantrone, an inventive polymeric composition represented by the following formula is formed:

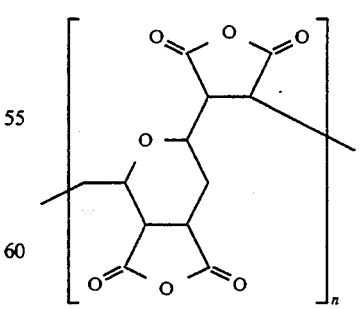

MVE

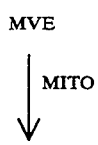

MITO

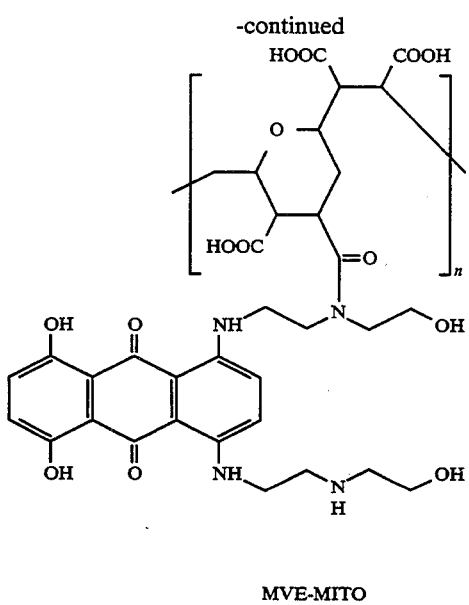

MVE-MITO

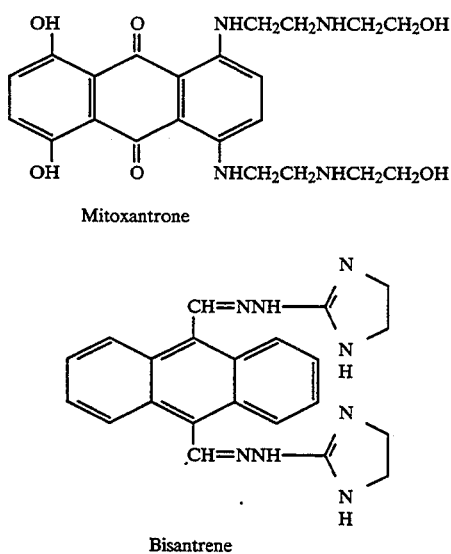

Mitoxantrone

Bisantrene

In the foregoing scheme, n has the value as set forth above and the anhydride moiety of the copolymer is converted to the free acid form by hydrolysis or salts thereof by neutralization. The anthracene antitumor agent is any suitable such compound having an amino group in the side chain for reaction with the maleic anhydride moiety of the polymer.

The compositions of the present invention may be prepared by mixing the anthracene antitumor agent with the hydrolyzed polymer in a pharmaceutically acceptable vehicle or the conjugated form may be readily prepared by reaction of the anthracene agent with the MVE copolymer in a suitable organic solvent such as 1-methyl-2-pyrrolidinone in the presence of a tertiary amine such as triethylamine. Conversion to the free acid or salt form of the anhydride moiety may be accomplished by conventional hydrolysis or neutralization.

DETAILED DESCRIPTION

Figure 1:
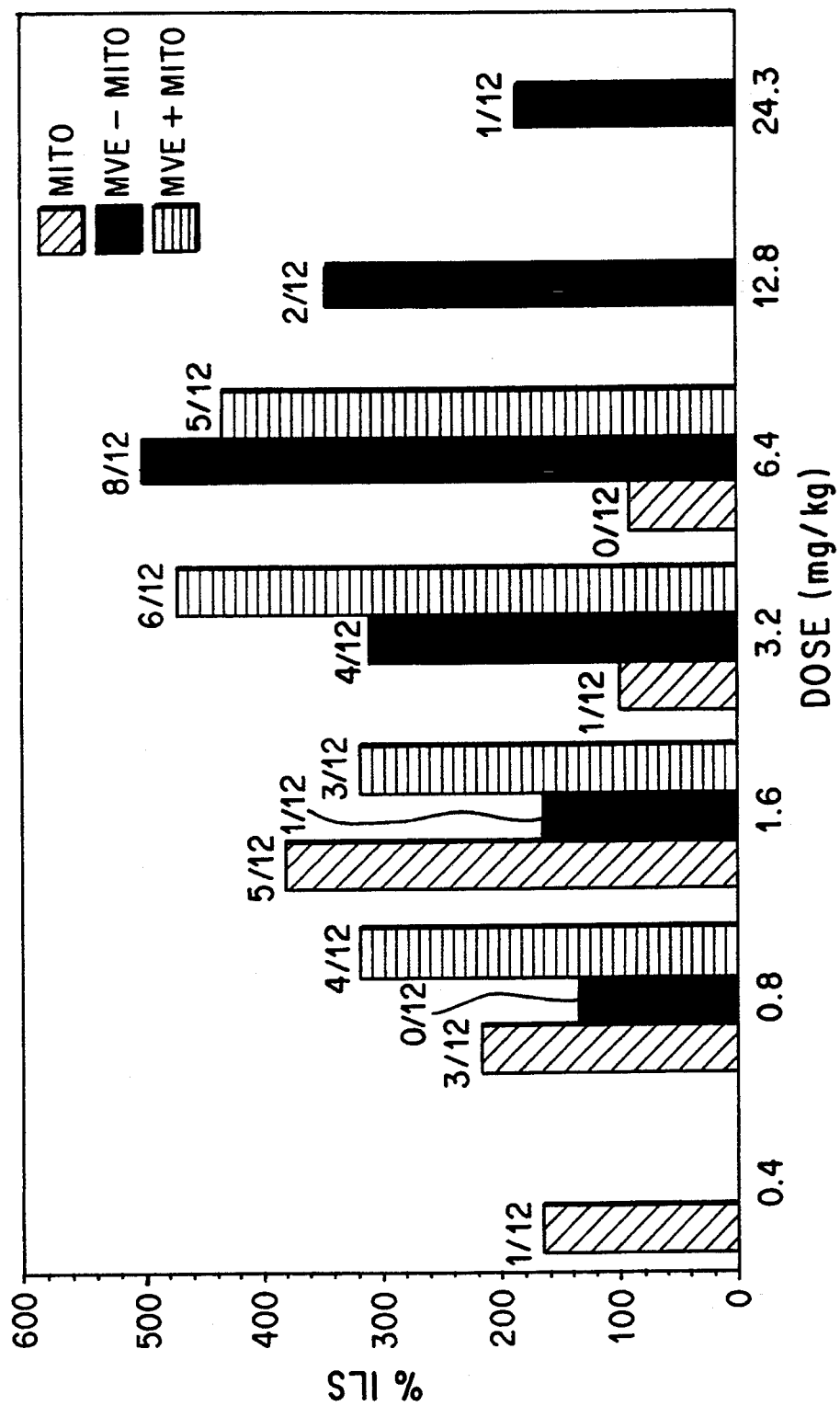
FIG. 1 is a graph illustrating the percent increase in life span (% ILS) of mice treated with free mitoxantrone as compared to the mitoxantrone-copolymer compositions of the present invention in the P388 tumor model.

The anthracene antitumor agents for use in the present invention are those known antitumor agents having an anthracene nucleus of which mitoxantrone and bisantrene are the best known examples. Mitoxantrone and bisantrene have the following structural formulae:

Mitoxantrone may be prepared in accordance with the disclosure of U.S. Pat. No. 4,197,249, hereby incorporated by reference into the present application. Bisantrene preparation is disclosed in U.S. Pat. No. 4,258,181, also incorporated by reference herein. These compounds are known as excellent antitumor agents in the treatment of various leukemias as well as other forms of cancer such as breast, colon and ovarian. The preferred compound for use in the present invention is mitoxantrone, but any anthracene antitumor agent having a reactive amino group in the molecule capable of forming an amide linkage with the carbonyl group of the maleic anhydride moiety of the MVE copolymer would be suitable for use in the present invention.

The MVE copolymer for use in the present invention is the copolymer expressed as general formula I. The copolymer may be prepared as known in art by the copolymerization of maleic anhydride and divinyl ether according to procedures described in the art, for example in U.S. Pat. No. 3,320,216. Those copolymers with an average molecular weight below 50,000, preferably in the range of 10,000–15,000 are suitable for use in the present invention. It is known that these MVE copolymers have a limited degree of inherent immunomodulating or antitumor activity themselves.

As stated above, the covalent conjugates of the present invention may be prepared by reacting the MVE copolymer with the anthracene antitumor agent in a suitable organic solvent such as N-methylpyrrolidone, dimethylsulfoxide, dimethylformamide and the like. The reaction is carried out in the presence of a proton scavenger such as a tertiary amine like triethylamine to form the amide linkage between the amino group of the anthracene agent and the carbonyl group of the maleic anhydride moiety of the MVE copolymer. Following hydrolysis to form the free acid form, it may be converted to the salt form with a variety of pharmacologically acceptable salt forming reagents containing a salt forming cation such as sodium, potassium, calcium, magnesium and the like. The organic solvent and low molecular weight organic compounds are removed by exhaustive dialysis against water.

When the compositions are administered in vivo, the amide linkage in the conjugate form is gradually hydrolyzed to release the free anti-tumor agent. This presumably leads to a slower release of the drug activity achieving favorable uptake by the tumor cells.

The active ingredients of the therapeutic compositions of the present invention induce regression and/or palliation of leukemia and related cancers in mammals when administered in amounts ranging from about 5 mg. to about 200 mg. per kilogram of body weight per day. A preferred dosage regimen for optimum results would be from about 5 mg. to about 50 mg. per kilogram of body weight per day, and such dosage units are employed that a total of from about 350 mg. to about 3.5 grams of the active compound for a subject of about 70 kg. of body weight are administered in a 24-hour period. This dosage regimen may be adjusted to provide the optimum therapeutic response. For example, several divided doses may be administered daily or the dose may be proportionally reduced as indicated by the exigencies of the therapeutic situation.

The active compounds may be administered parenterally or intraperitoneally. Solutions of the active compound as free acid or pharmacologically acceptable salt can be prepared in water suitably mixed with a surfactant such as hydroxypropylcellulose. Dispersions can also be prepared in glycerol, liquid polyethylene gylcols, and mixtures thereof and in oils. Under ordinary conditions of storage and use, these preparations contain a preservative to prevent the growth if microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride.

Sterile injectable solutions are prepared by incorporating the active compound in the required amount in the appropriate solvent with various of the other ingredients enumerated above, as required, followed by filtered sterilization. Generally, dispersions are prepared by incorporating the various sterilized active ingredient into a sterile vehicle which contains the basic dispersion medium and the required other ingredients for those enumerated above. In the case of sterile powders for the preparation of sterile injectable solutions, the preferred methods of preparation are vacuum drying and the freeze-drying technique which yield a powder of the active ingredient plus any additional desired ingredient from a previously sterile-filtered solution thereof.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active material calculated to produce the desired therapeutic effect in association with the required pharmaceutical carrier. The specification for the novel dosage unit forms of the invention are dictated by and directly dependent on (a) the unique characteristics of the active material and the particular therapeutic effect to be achieved, and (b) the limitations inherent in the art of compounding such an active material for the treatment of disease in living subjects having a diseased condition in which bodily health is impaired as herein disclosed in detail.

The principal active ingredient is compounded for convenient and effective administration in effective amounts with a suitable pharmaceutically-acceptable carrier dosage form can, for example, contain the principal active compound in amounts ranging from about 0.1 to about 400 mg., with from about one to about 30 mg. being preferred. Expressed in proportions, the active compound is generally present in from about 0.1 to about 400 mg./ml. of carrier. In the case of compositions containing supplementary active ingredients, the dosages are determined by reference to the usual dose and manner of administration of the said ingredients.

Regression and palliation of cancers are attained, for example, using intravenous administration. A single intravenous dosage or repeated daily dosages can be administered. Daily dosages up to about 5 to 10 days are often sufficient. It is also possible to dispense one daily dosage or one dose on alternate or less frequent days. As can be seen from the dosage regimens, the amount of principal active ingredient administered is a sufficient amount to the aid regression and palliation of the leukemia or the like, in the absence of excessive deleterious side effects of a cytoxic nature to the hosts harboring the cancer. As used herein, cancer disease means blood malignancies such as leukemia, as well as other solid and non-solid malignancies such as the melanocarcinomas, lung carcinomas, mammary tumors, colon tumors and ovarian tumors. By regression and palliation is meant arresting or retarding the growth of the tumor or other manifestation of the disease compared to the course of the disease in the absence of treatment.

The novel compositions of the present invention possess the property of inducing regression and/or palliation of cancer diseases in mammals as established by the following tests wherein mitoxantrone was used as the anthracene antitumor agent in the composition.

Lymphocytic Leukemia P388 test

In the P388 murine leukemia tests, male BDF1 mice weighing 18 to 21 g were injected intraperitoneally (ip) with $1 \times 10^6$ P388 tumor cells on day 0 of the test. Drugs were administered ip at days 1, 5 and 9 post tumor inoculation. Six to twelve mice per group were used. The effect on survival was expressed as % ILS which was calculated as follows: $ILS = [(T/C) - 1] \times 100$, where T/C is the median survival time (MST) of mice in the treated group (T) divided by the MST of the placebo treated control group (C). A value of % ILS equivalent to 25% or greater indicated positive drug activity.

The MVE polymeric derivative of mitoxantrone was testing for its effect against the P388 tumor in a dose range of 0.8 to 24.3 mg./kg. and showed dose dependent antitumor activity (FIG. 1.) MVE copolymer itself, even though it has been reported to have immunostimulating and antitumor activity, in our hands produced only a 10% ILS when tested at a dose equivalent to that contained in the highest polymeric drug dose. Free mitoxantrone was toxic and lees active than either the MVE+MITO mixture or MVE−MITO conjugate at doses over 1.6 mg./kg. of drug equivalent dose. Moreover, the activity of the polymeric drug at doses above 3.2 mg./kg. was greater than free mitoxantrone at any of the doses tested and was greater than would have been expected by merely adding the activity of free mitoxantrone and that of the copolymer itself. The optimal dose of the polymeric drug was 6.4 mg/kg (% ILS>500%) with many long-term survivors (8 mice out of 12 mice survived at day 60).

H207 Ovarian Tumor Model Test

Tumor fragments were prepared by ascetical removal of tumors followed by mince to 2–5 mm pieces. Female nude-nude mice (from Harlan Sprague Dawley) weighing 21 to 23 g were injected subcutaneously with 5–6 tumor fragments on day 0 of the test. When tumors reached the size of 50–150 mg (7–8 days post tumor inoculation), mice were treated with drugs at days 8, 12 and 16 post tumor inoculation. Tumors were measured with calipers once per week and tumor masses were calculated according to formula L×W²/2. A value of T/C×1004 equivalent to 424 or less indicated positive drug activity.

Figure 2:
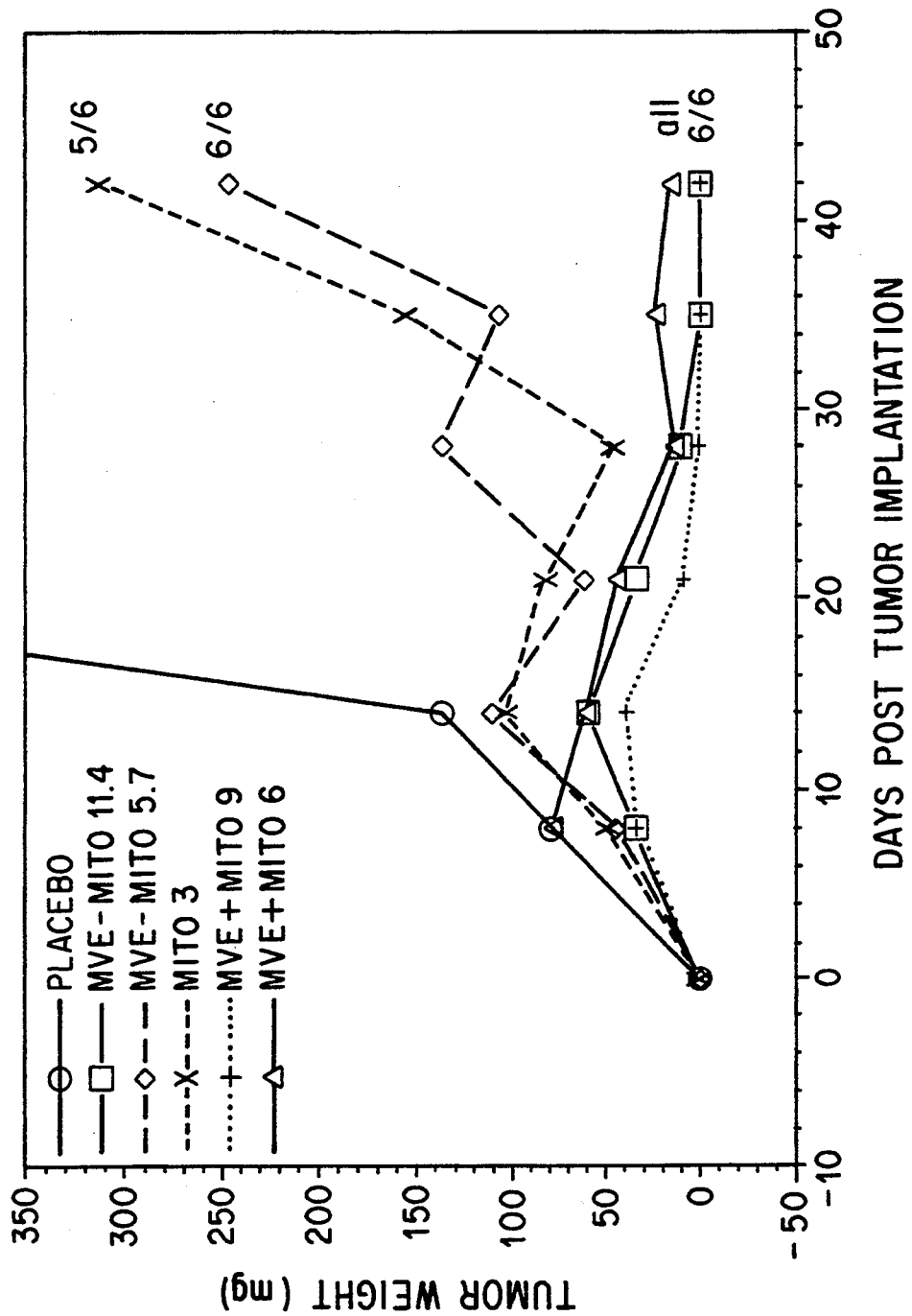
FIG. 2 is a graph illustrating the results of in vivo testing of free mitoxantrone as compared to the mitoxantrone-copolymer compositions of the present invention in the H207 ovarian mouse tumor model.

The MVE polymeric derivative of mitoxantrone was testing against human ovarian H207 carcinoma in mice and was active in a dose range of 5.7 to 17.1 mg/kg. Free mitoxantrone suppressed the tumor growth to only 34 of the placebo at day 35 post tumor implantation, but started to show toxicity with 83% of mice survived. In contrast to free mitoxantrone, mice treated with MVE-mitoxantrone conjugate in doses of 5.7–11.4 mg/kg all survived without tumor. When mice treated with MVE-mitoxantrone conjugate at a dose as high as 17.1 mg/kg, mice were tumor-free with a survival rate of 67%. Therefore, derivatization of mitoxantrone with MVE increases the therapeutic window of mitoxantrone. Similar results were also observed on mice treated with physical mixtures of mitoxantrone and hydrolyzed MVE polymer. Mice treated with the physical mixture of mitoxantrone and the hydrolyzed MVE copolymer all survived without tumor. MVE copolymer itself was not active (T/C=94%) when tested at a dose equivalent to that contained in the highest polymeric drug dose. FIG. 2 shows the increase in tumor weight and survival rates for mice treated according to the foregoing protocol.

This invention will be described in greater detail in conjunction with the following specific examples.

EXAMPLE 1

Fifty milligrams of divinyl ether/maleic anhydride (MVE) copolymer (MW 10,000) were dissolved in 0.4 ml of 1-methyl-2-pyrrolidinone. It was then reacted with 100 mg. of mitoxantrone hydrochloride salt dissolved in 1.75 ml of 1-methyl-2-pyrrolidinone and 0.16 ml of triethylamine. After the reaction proceeded at room temperature overnight, 7.69 ml of water were added and stirred for one hour. The reaction product was purified by PD-10 columns and subsequently by extensive dialysis. After filtration through a 0.45 μm filter, 18.25 ml of a deep blue solution was obtained. TLC analysis of this blue solution (silica gel, THF:water:HOAc=55:30:15) showed only a blue spot at the origin of the plate, indicating mitoxantrone was covalently linked to MVE copolymer and no free mitoxantrone was present in the product. UV analysis of the product indicated an average of 18 molecules of mitoxantrone per molecule of MVE copolymer. The mitoxantrone content was 44.5% by weight.

I claim:

1. A pharmaceutical composition comprising a covalent conjugate of mitoxantrone with a copolymeric moiety of divinyl ether and maleic anhydride in association with a pharmaceutically acceptable carrier, said conjugate being a reaction product prepared by reacting a divinyl ether/maleic anhydride copolymer (MVE) with mitoxantrone in a suitable organic solvent in the presence of a tertiary amine, said reaction product showing a blue spot at the origin of the plate on thin layer chromatographic analysis and exhibiting an average of 18 molecules of mitoxantrone per molecule of MVE copolymer on UV analysis.

2. The pharmaceutical composition according to claims 1, wherein the copolymeric moiety of maleic anhydride and divinyl ether has a molecular weight of 50,000 or less.

3. A method of treating solid tumors in a mammal which comprises administering to said mammal a therapeutically effective amount of a composition in accordance with claim 1.

4. A method of inducing regression of leukemia cell growth in a mammal which comprises administering to said mammal a therapeutically effective amount of a composition in accordance with claim 1.

* * * * *